United States Patent
Neumann

(10) Patent No.: US 12,142,362 B2
(45) Date of Patent: Nov. 12, 2024

(54) SYSTEM AND METHOD FOR GENERATING A THYROID MALADY NOURISHMENT PROGRAM

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 305 days.

(21) Appl. No.: 17/221,442

(22) Filed: Apr. 2, 2021

(65) Prior Publication Data

US 2022/0319663 A1    Oct. 6, 2022

(51) Int. Cl.
| | |
|---|---|
| G16H 20/60 | (2018.01) |
| G16H 10/60 | (2018.01) |
| G16H 50/20 | (2018.01) |
| G16H 50/30 | (2018.01) |
| G16H 50/70 | (2018.01) |
| A61B 5/00 | (2006.01) |

(52) U.S. Cl.
CPC ............ *G16H 20/60* (2018.01); *G16H 10/60* (2018.01); *G16H 50/20* (2018.01); *G16H 50/30* (2018.01); *G16H 50/70* (2018.01); *A61B 5/4227* (2013.01)

(58) Field of Classification Search
CPC ........ G16H 20/60; G16H 50/30; G16H 10/60; G16H 50/70; A61B 5/4227
See application file for complete search history.

(56) References Cited

U.S. PATENT DOCUMENTS

| | | | |
|---|---|---|---|
| 2016/0012748 A1* | 1/2016 | Donavon | G09B 19/0092 434/225 |
| 2016/0339086 A1* | 11/2016 | Cohen | A61K 33/32 |
| 2018/0271440 A1* | 9/2018 | Yun | G16H 50/30 |
| 2024/0130690 A1* | 4/2024 | MacIntyre | A61B 5/14532 |

FOREIGN PATENT DOCUMENTS

WO    WO-2018031991 A1 *    2/2018    ........... G06F 19/326

OTHER PUBLICATIONS

Li, Y., Zhou, G., Ozaki, T. et al. Distinct histopathological features of Hashimoto's thyroiditis with respect to IgG4-related disease. Mod Pathol 25, 1086-1097 (2012). https://doi.org/10.1038/modpathol.2012.68 (Year: 2012).*

(Continued)

*Primary Examiner* — Jason S Tiedeman
*Assistant Examiner* — Tristan Isaac Evans
(74) *Attorney, Agent, or Firm* — Caldwell Intellectual Property Law

(57) ABSTRACT

A system for generating a thyroid malady nourishment program includes a computing device, the computing device configured to obtain a vigor element, identify a thyroid status as a function of the vigor element, wherein producing the thyroid status further comprises obtaining a homeostatic element from a vigor database, producing a thyroid enumeration as a function of the vigor element, and identifying the thyroid status as a function of the homeostatic element and the thyroid enumeration using a status machine-learning model, determine an edible as a function of the thyroid status, and generate a nourishment program as a function of the edible.

20 Claims, 7 Drawing Sheets

(56) References Cited

OTHER PUBLICATIONS

Chang CY, Lei YF, Tseng CH, Shih SR. Thyroid segmentation and volume estimation in ultrasound images. IEEE Trans Biomed Eng. Jun. 2010;57(6):1348-57. doi: 10.1109/TBME.2010.2041003. Epub Feb. 17, 2010. PMID: 20172782. (Year: 2010).*

Kistenev et al., Analysis of Collagen Spatial Structure Using Multiphoton Microscopy and Machine Learning Methods, Biochemistry (Moscow), 2019, vol. 84, Suppl. 1, pp. S108-S123, 2019 (Year: 2019).*

Soh. Clinical Chemistry. Laboratory Testing in Thyroid Conditions—Pitfalls and Clinical Utility. Ann Lab Med 2019;39:3014. (Year: 2019).*

Type: PDF, Journal of Immunology Research Title: Exploring Systemic Autoimmunity in Thyroid Disease Subjects by: Thushani Siriwardhane Date: Jul. 18, 2018.

Type: PDF, Frontiers in Endocrinology Title: Thyroid hormones, T3 and T4, in the brain by: Amy C. Schroeder & Martin L. Privalsky Date: Mar. 31, 2014.

\* cited by examiner

SYSTEM AND METHOD FOR GENERATING A THYROID MALADY NOURISHMENT PROGRAM

FIELD OF THE INVENTION

The present invention generally relates to the field of artificial intelligence. In particular, the present invention is directed to a system and method for generating a thyroid malady nourishment program.

BACKGROUND

Current edible suggestion systems do not account for the presence of one or more thyroid functions of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect, a system for generating a thyroid malady nourishment program includes a computing device, the computing device configured to obtain a vigor element, identify a thyroid status as a function of the vigor element, wherein producing the thyroid status further comprises obtaining a homeostatic element from a vigor database, producing a thyroid enumeration as a function of the vigor element, and identifying the thyroid status as a function of the homeostatic element and the thyroid enumeration using a status machine-learning model, determine an edible as a function of the thyroid status, and generate a nourishment program as a function of the edible.

In another aspect, a method for generating a thyroid malady nourishment program includes obtaining, by a computing device, a vigor element, identifying, by the computing device, a thyroid status as a function of the vigor element, wherein identifying the thyroid status further comprises obtaining a homeostatic element from a vigor database, producing a thyroid enumeration as a function of the vigor element, and identifying the thyroid status as a function of the homeostatic element and the thyroid enumeration using a status machine-learning model, determining, by the computing device, an edible as a function of the thyroid status, and generating, by the computing device, a nourishment program as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a thyroid malady nourishment program. In an embodiment, this disclosure obtains a vigor element. Aspects of the present disclosure can be used to identify a thyroid status. This is so, at least in part, because this disclosure utilizes a machine-learning model. Aspects of the present disclosure can also be used to determine an edible. Aspects of the present disclosure allow for generating a nourishment program as a function of the edible. Exemplary embodiments illustrating aspects of the present disclosure are described below in the context of several specific examples.

Figure 1:
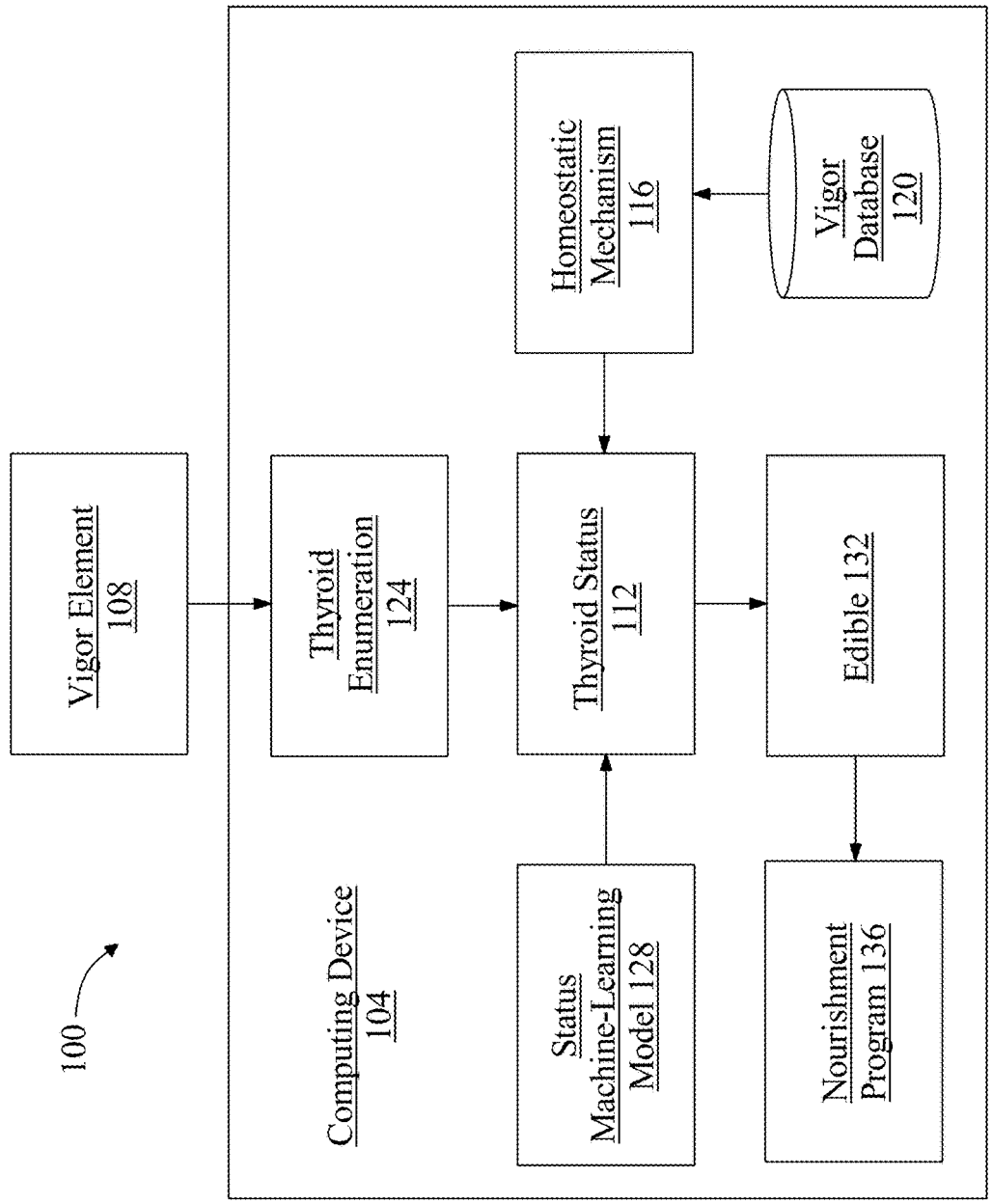
FIG. 1 is a block diagram illustrating an exemplary embodiment of a system for generating a thyroid malady nourishment program.

Referring now to FIG. 1, an exemplary embodiment of a system 100 for generating a thyroid malady nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a vigor element 108. As used in this disclosure an "vigor element" is an element of data associated with an individual's biological system that denotes a health status of a thyroid system, wherein a health status is a measure of the relative level of physical well-being. In an embodiment, vigor element 108 may denote one or more health status's of an individual's endocrine system. As used in this disclosure an "endocrine system" is a chemical messenger system of an individual's body. For example, and without limitation, endocrine system may include one or more chemical messages associated with growth, development, metabolism, reproduction, and the like thereof. In an embodiment, computing device 104 may obtain vigor element 108 as a function of receiving a proneness indicator. As used in this disclosure a "proneness indicator" is an element of data associated with the likelihood for a thyroid system modification to occur. For example, and without limitation, proneness indicator may denote that an individual has a high likelihood for a thyroid system modification to occur. In an embodiment proneness indicator may include a genetic element. As used in this disclosure a "genetic element" is an element of data associated with the composition of DNA unique to each individual. For example, and without limitation, genetic element may include an element of data denoting the individual has a predisposition for thyroid system modifications as a function of one or more genes such as, but not limited to, DUOX2, SLC5A5, TG, TPO, and the like thereof. In an embodiment, proneness indicator may include a mutation indicator. As used in this disclosure a "mutation indicator" is an element that denotes a likelihood for an individual to have a mutation of the thyroid system. For example, and without limitation, mutation indicator may include one or more propensities for mutation due to radiation, electromagnetic waves, chemicals, infectious agents and the like thereof. Mutation indicator may include one or more epigenetic elements. As used in this disclosure an "epigenetic element" is an element relating to the change in the thyroid system of an individual as a function of one or more external factors. For example, and without limitation, epigenetic element may include one or more external factors such as traumatic events, illicit drug use, environmental influences, and the like thereof. Mutation indicator may include an inheritance element. As used in this disclosure an "inheritance element" is an element associated with inherited DNA from one or more parents of an individual. For example, and without limitation inheritance element may indicate that a particular region of an individual's DNA was inherited from a mother. As a further non-limiting example, inheritance element may indicate that a particular region of an individual's DNA was inherited from a father. Inheritance element may include one or more lineages, such as a DNA segment from a parent, grandparent, great grandparent, and the like thereof. Inheritance element may be associated with a diploid and/or haploid inheritance of a region of DNA. For example, a first region may be only inherited from a first parent, wherein a second region may be a combination of DNA inherited from the first parent and a second parent. Additionally or alternatively, proneness indicator may include an element of data associated with a dietary habit. As used in this disclosure a "dietary habit" is a habit of an individual to consume edibles. For example, and without limitation, an individual that consumes high quantities of iodine every day may have a likelihood for developing a thyroid system modification.

In an embodiment, and still referring to FIG. 1, vigor element 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Vigor element 108 may include a biological sampling device. Vigor element 108 may include one or more biomarkers. As used in this disclosure a "biomarker" is a molecule and/or chemical that identifies the status of an individual's thyroid system. As a non-limiting example, vigor elements may include, triiodothyronine (TT3), thyroid-stimulating hormone (TSH), free thyroxine (FT4), thyroglobulin (Tg), anti-thyroglobulin antibody (TgAb), anti-thyroperoxidase antibody (TPOAb), and the like thereof. As a further non-limiting example, vigor element 108 may include datum from one or more devices that collect, store, and/or calculate one or more lights, voltages, currents, sounds, chemicals, pressures, and the like thereof that are associated with the individual's health status. For example, and without limitation a device may include a magnetic resonance imaging device, magnetic resonance spectroscopy device, x-ray spectroscopy device, computerized tomography device, ultrasound device, electroretinogram device, electrocardiogram device, ABER sensor, mass spectrometer, and the like thereof. Additionally or alternatively, vigor element 108 may include any vigor element 108 used as a vigor element as described in U.S. Nonprovisional application Ser. No. 17/128,095, filed on Dec. 29, 2020, and entitled "METHODS AND SYSTEMS FOR DIETARY COMMUNICATIONS USING INTELLIGENT SYSTEMS REGARDING ENDOCRINAL MEASUREMENTS," the entirety of which is incorporated herein by reference.

Still referring to FIG. 1, computing device 104 may obtain vigor element 108 by receiving an input. As used in this disclosure an "input" is an element of datum that is obtained by an individual relating to the health status of the thyroid system. As a non-limiting example input may include a questionnaire and/or survey that identifies a feeling of pain, headache, fever, lethargy, loss of appetite, tenderness, malaise, redness, muscle weakness, and the like thereof. Input may include data from an informed advisor as a function of a medical assessment, wherein a "medical assessment" is an evaluation and/or estimation of the individual's thyroid system. As used in this disclosure "informed advisor" is an individual that is skilled in the health and wellness field. As a non-limiting example an informed advisor may include a medical professional who may assist and/or participate in the medical treatment of an individual's thyroid system including, but not limited to, thyroidologists, family physicians, endocrinologists, gastroenterologists, internists, oncologists, pediatricians, cardiologists, geneticists, neurologists, physical therapists, primary care providers, and the like thereof. As a non-limiting example input may include an informed advisor that enters a medical assessment comprising a physical exam, neurologic exam, blood test, urine test, imaging test, cellular and/or chemical analysis, genetic test, measurement, visual examination, and the like thereof. As a further non-limiting example, input may include a cognitive assessment. As used in this disclosure a "cognitive assessment" is an evaluation and/or estimation of the cognitive functions of an individual. For example, and without limitation, a cognitive assessment may include one or more assessments of memory, behavior, motor function, emotions, and the like thereof. Cognitive assessment may identify one or more feelings and/or cognitive functions of an individual such as, but not limited to, feeling nervous, on edge, restless, unsettled, stressed, surprised, creative, imaginative, daring, adventurous, high energy, low energy, angry, calm, comfortable, contentment, peace, relaxed, loveable, slow moving, fast moving, irritable, impulsive, dull, obsessing, and the like thereof. Cognitive assessment may additionally or alternatively include any cognitive assessment used as a cognitive assessment as described in U.S. Nonprovisional application Ser. No. 17/128,120, filed on Dec. 29, 2020, and entitled "METHODS AND SYSTEMS FOR NOURISHMENT REFINEMENT USING PSYCHIATRIC MARKERS," the entirety of which is incorporated herein by reference. In another embodiment, and without limitation, input may include one or more inputs from a family member. For example, and without limitation, a brother, sister, mother, father, cousin, aunt, uncle, grandparent, child, friend, and the like thereof may enter to computing device 104 that an individual has an increased appetite and/or is not regulating their temperature properly.

Still referring to FIG. 1, computing device 104 identifies a thyroid status 112. As used in this disclosure a "thyroid status" is a status and/or estimation of an individual's thyroid system. For example, and without limitation, thyroid status 112 may denote that an individual's thyroid function is outputting lower than normal T3 concentrations. As a further non-limiting example, status 112 may denote that an individual's thyroid function is increasing basal metabolic rate, pulse, heartbeat, and/or sexual function. As a further non-limiting example, thyroid status 112 may denote that an individual's thyroid system is altering and/or modifying an individual's sleep and/or thought processes. Computing device 104 identifies thyroid status as a function of obtaining a homeostatic element 116. As used in this disclosure a "homeostatic element" is an element of datum representing a mechanism that adjusts an individual's health system to maintain a constant and/or balanced health system, such as but not limited to a homeostatic mechanism and/or a homeostasis. In an embodiment and without limitation, homeostatic element 116 may include a plurality of parts and/or mechanisms such as a receptor, control center, effector, and the like thereof. For example, and without limitation, homeostatic element 116 may include an element of datum denoting the status of homeostasis. For example, and without limitation, homeostatic element 116 may include datum denoting the status of homeostasis such as, but not limited to, maintaining equilibrium of an individual's body temperature, fluid balance, pH range, and the like thereof. As a further non-limiting example, homeostatic element 116 may include datum denoting the status of homeostasis such as, but not limited to, regulation and/or control of core temperatures, blood glucose, iron levels, copper regulation, blood gas levels, blood oxygen content, calcium levels, sodium concentrations, potassium concentrations, fluid balances, energy balance, and the like thereof. Additionally or alternatively, homeostatic element 116 may include a positive feedback loop. As used in this disclosure a "positive feedback loop" is a process where an output of a reaction leads to an increase of the reaction. In an embodiment homeostatic element 116 may include a negative feedback loop, wherein a negative feedback loop is described in detail below, in reference to FIG. 4.

Still referring to FIG. 1, homeostatic element 116 is obtained as a function of a vigor database 120. As used in this disclosure a "vigor database" is a database containing one or more homeostatic elements. Vigor database 120 may be implemented, without limitation, as a relational databank, a key-value retrieval databank such as a NOSQL databank, or any other format or structure for use as a databank that a person skilled in the art would recognize as suitable upon review of the entirety of this disclosure. Vigor database 120 may alternatively or additionally be implemented using a distributed data storage protocol and/or data structure, such as a distributed hash table or the like. Vigor database 120 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Vigor database 120 may include a peer review. As used in this disclosure a "peer review" is a source that establishes a guideline as a function of an evaluation conducted by one or more people with similar competencies. Peer review may identify one or more homeostatic elements as a function of a peer review evaluation conducted by one or more informed advisors with similar competencies. As a non-limiting example peer review may include professional peer reviews, scholarly peer reviews, government peer reviews, medical peer reviews, technical peer reviews, and the like thereof. Vigor database 120 may include an informed advisor association. Informed advisor association may identify one or more homeostatic elements as a function of one or more committees, organizations, and/or groups that at least determine and/or organize homeostatic elements. As a non-limiting example informed advisor association may include the American Medical Association, Endocrine Society, American Association Clinical Endocrinology, Society for Endocrinology, American Thyroid Association, The Hormone Health Network, American Board of Internal Medicine, and the like thereof. Vigor database 120 may include a medical website. Medical website may identify one or more homeostatic elements as a function of one or more online and/or web-based medical recommendations. As a non-limiting example medical website may include Medline Plus, Drugs.com, Mayo Clinic, Orphanet, Medgadget, WebMD, Health.gov, SPM ePatients blog, and the like thereof.

Still referring to FIG. 1, computing device 104 produces a thyroid enumeration 124 as a function of vigor element 108. As used in this disclosure a "thyroid enumeration" is a measurable value associated with the health status of the individual's thyroid gland, wherein a thyroid gland is an endocrine gland in the neck consisting of two connected lobes are suprarenal glands that produce a plurality of hormones, as described in detail below, in reference to FIG. 2. For example, and without limitation, thyroid gland may produce one or more hormones to regulate an individual's metabolism, immune system, blood pressure, basal metabolic rate, body temperature, circulatory system, neurological system, sexual function, sleep patterns, cognitive functions, menstrual cycles, and the like thereof. As a non-limiting example, thyroid enumeration 124 may be a value of 45 for a thyroid health status of "healthy." As a further non-limiting example, thyroid enumeration 124 may be a value of 75 for a thyroid health status of diseased, ill, and/or unwell. In an embodiment, thyroid enumeration 124 may be produced as a function of one or more measures of endocrine elements. As used in this disclosure an "endocrine element" is an element of endocrine datum representing one or more measures of thyroid health. For example, and without limitation, endocrine element may include one or more endocrine hormones such as aldosterone, corticosteroid, antidiuretic hormone, adrenocorticotropic hormone, growth hormone, luteinizing hormone, follicle-stimulating hormone, oxytocin, prolactin, thyroid-stimulating hormone, renin, angiotensin, erythropoietin, glucagon, insulin, estrogen, progesterone, parathyroid hormone, thyroid hormone, epinephrine, norepinephrine, testosterone, melatonin, growth hormone releasing hormone, thyrotropin releasing hormone, gonadotropin releasing hormone, corticotrophin releasing hormone, humoral factors, and the like thereof. For example, and without limitation, thyroid enumeration 124 may be determined to be 34 for an endocrine element of 10 ng/dL of aldosterone in an individual's plasma. Additionally or alternatively, endocrine element may include any endocrine element used as an endocrine element as described in U.S. Nonprovisional application Ser. No. 17/136,095, filed on Dec. 29, 2020, and entitled "METHODS AND SYSTEMS FOR DIETARY COMMUNICATIONS USING INTELLIGENT SYSTEMS REGARDING ENDOCRINAL MEASUREMENTS," the entirety of which is incorporated herein by reference. Computing device 104 may produce thyroid enumeration 124 as a function of determining an origin of malfunction. As used in this disclosure an "origin of malfunction" is one or more origination locations of the thyroid gland modification. For example, and without limitation, an origin of malfunction may denote that an overproduction of thyroid stimulating hormone originated from a hypothalamus overstimulation and not from a malfunction at the thyroid gland. As a further non-limiting example, origin of malfunction may denote that a decreased cognitive function originated from a malfunction of reduced T3 in the thyroid gland.

Still referring to FIG. 1, computing device 104 may produce thyroid enumeration 124 as a function of vigor element 108 and origin of malfunction using an origin machine-learning model. As used in this disclosure an "origin machine-learning model" is a machine-learning model to produce a thyroid enumeration output given vigor elements and origins of malfunction as inputs; this is in contrast to a non-machine learning software program where the commands to be executed are determined in advance by a user and written in a programming language. Origin machine-learning model may include one or more origin machine-learning processes such as supervised, unsupervised, or reinforcement machine-learning processes that computing device 104 and/or a remote device may or may not use in the determination of thyroid enumeration 124. As used in this disclosure "remote device" is an external device to computing device 104. An origin machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train origin machine-learning process as a function of an origin training set. As used in this disclosure "origin training set" is a training set that correlates a vigor element and/or origin of malfunction to a thyroid enumeration. For example, and without limitation, a vigor element of calcitonin and an origin of malfunction of the hypothalamus may relate to a thyroid enumeration of 17. As a further non-limiting example, a vigor element of T4 and an origin of malfunction of the thyroid gland may relate to a thyroid enumeration of 82. Origin training set may be received as a function of user-entered valuations of vigor elements, origins of malfunction, and/or thyroid enumerations. Computing device 104 may receive origin training set by receiving correlations of vigor elements, and/or origins of malfunction that were previously received and/or determined during a previous iteration of determining thyroid enumerations. Origin training set may be received by one or more remote devices that at least correlate a vigor element and/or origin of malfunction to a thyroid enumeration, wherein a remote device is an external device to computing device 104, as described above. Origin training set may be received in the form of one or more user-entered correlations of a vigor element and/or origin of malfunction to a thyroid enumeration. A user may include an informed advisor, wherein an informed advisor may include, without limitation, thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive origin machine-learning model from a remote device that utilizes one or more origin machine learning processes, wherein a remote device is described above in detail. For example, and without limitation, a remote device may include a computing device, external device, processor, and the like thereof. Remote device may perform the origin machine-learning process using the origin training set to generate thyroid enumeration 124 and transmit the output to computing device 104. Remote device may transmit a signal, bit, datum, or parameter to computing device 104 that at least relates to thyroid enumeration 124. Additionally or alternatively, the remote device may provide an updated machine-learning model. For example, and without limitation, an updated machine-learning model may be comprised of a firmware update, a software update, an origin machine-learning process correction, and the like thereof. As a non-limiting example a software update may incorporate a new vigor element that relates to a modified origin of malfunction. Additionally or alternatively, the updated machine learning model may be transmitted to the remote device, wherein the remote device may replace the origin machine-learning model with the updated machine-learning model and determine the thyroid enumeration as a function of the vigor element using the updated machine-learning model. The updated machine-learning model may be transmitted by the remote device and received by computing device 104 as a software update, firmware update, or corrected origin machine-learning model. For example, and without limitation origin machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

In an embodiment and without limitation, origin machine-learning model may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n}a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 identifies thyroid status 112 as a function of thyroid enumeration 124 and homeostatic element 116 using a status machine-learning model 128. As used in this disclosure, a "status machine-learning model" is a machine-learning model to produce thyroid status 112 output given thyroid enumeration 124 and/or homeostatic element 116 as inputs; this is in contrast to a non-machine learning software program where the commands to be executed are determined in advance by a user and written in a programming language. Status machine-learning model 128 may include one or more status machine-learning processes such as supervised, unsupervised, or reinforcement machine-learning processes that computing device 104 and/or a remote device may or may not use in the determination of thyroid status 112. A status machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train status machine-learning process as a function of a status training set. As used in this disclosure, a "status training set" is a training set that correlates at least a homeostatic element and a thyroid enumeration to a thyroid status. As a non-limiting example a homeostatic element of a bone growth may be relate to a thyroid enumeration of 23 for calcitonin production wherein a thyroid status of decreasing and/or reduced thyroid functioning may be outputted. The status training set may be received as a function of user-entered valuations of homeostatic elements, thyroid enumerations, and/or thyroid statuses. Computing device 104 may receive status training set by receiving correlations of homeostatic elements and/or thyroid enumerations that were previously received and/or determined during a previous iteration of determining thyroid statuses. The status training set may be received by one or more remote devices that at least correlate a homeostatic element and/or thyroid enumeration to a thyroid status, wherein a remote device is an external device to computing device 104, as described above. The status training set may be received in the form of one or more user-entered correlations of a homeostatic element and thyroid enumeration to a thyroid status. Additionally or alternatively, a user may include an informed advisor, wherein an informed advisor may include, without limitation, thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive status machine-learning model 128 from the remote device that utilizes one or more status machine learning processes, wherein a remote device is described above in detail. For example, and without limitation, a remote device may include a computing device, external device, processor, and the like thereof. The remote device may perform the status machine-learning process using the status training set to generate thyroid status and transmit the output to computing device 104. The remote device may transmit a signal, bit, datum, or parameter to computing device 104 that at least relates to thyroid statuses. Additionally or alternatively, the remote device may provide an updated machine-learning model. For example, and without limitation, an updated machine-learning model may be comprised of a firmware update, a software update, a status machine-learning process correction, and the like thereof. As a non-limiting example a software update may incorporate a new homeostatic element that relates to a modified thyroid enumeration. Additionally or alternatively, the updated machine learning model may be transmitted to the remote device, wherein the remote device may replace the status machine-learning model with the updated machine-learning model and determine the thyroid status as a function of the homeostatic element using the updated machine-learning model. The updated machine-learning model may be transmitted by the remote device and received by computing device 104 as a software update, firmware update, or corrected status machine-learning model. For example, and without limitation status machine-learning model may utilize a Naïve bayes machine-learning process, wherein the updated machine-learning model may incorporate decision tree machine-learning process. Additionally or alternatively, status machine-learning model 128 may determine the thyroid status as a function of one or more classifiers, wherein a classifier is described above in detail.

In an embodiment, and still referring to FIG. 1, computing device may determine a homeostatic divergence as a function of vigor element 108 and homeostatic element 116. As used in this disclosure a "homeostatic divergence" is a quantitative value comprising the magnitude of divergence of vigor element 108 from a homeostatic element 116. As a non-limiting example, homeostatic divergence may be 73 for a homeostatic element that may denote that 200-400 pg/mL of calcitonin should be produced, wherein vigor element 108 identifies that an individual has produced 75 pg/mL. Homeostatic divergence may be determined as a function of vigor element 108, homeostatic mechanism, and a divergence threshold. As used in this disclosure a "divergence threshold" is a parameter that identifies one or more variance limits of the vigor element from homeostatic element. As a non-limiting example, divergence threshold may determine that an individual is imbalanced with respect to a homeostatic element when a vigor element for T3 exceeds 10 mcg. Divergence threshold may be obtained as a function of a query denoting a plurality of factors of an individual. For example and without limitation, one or more factors of an individual may include age, sex, height, weight, income, physical activity, demographics, and the like thereof. As a further non-limiting example, one or more factors may include one or more body types, such as but not limited to an ectomorph type, mesomorph type, endomorph type, and the like thereof.

Still referring to FIG. 1, computing device 104 may a statistical deviation as a function of homeostatic divergence. As used in this disclosure a "statistical deviation" is a measure of difference between the observed homeostatic divergence and a statistical value computed from a plurality of values in a sample and/or population. For example, and without limitation, a statistical value may be a calculated mean, mode, median, probability distribution, and the like thereof of a plurality of previous vigor elements and/or inputs from an individual. As a further non-limiting example, a statistical value may be a calculated mean, mode, median, probability distribution, and the like thereof of a plurality of previous vigor elements and/or inputs from a group of individuals. For example, and without limitation, a group of individuals may include one or more groups denoted by demographics, such as but not limited to, race, age, ethnicity, gender, marital status, income, education, employment, and the like thereof. In an embodiment, and without limitation, statistical deviation may include an unsigned deviation, mean signed deviation, dispersion, normalization, standard deviation, average absolute deviation, median absolute deviation, maximum absolute deviation, and the like thereof. As a non-limiting example, homeostatic divergence may be one standard deviation from a statistical value representing a mean brain development rate of individuals ranging from 10-20 years old.

In an embodiment, and still referring to FIG. 1, computing device may determine a status movement. As used in this disclosure a "status movement" is a trend and/or movement of an individual's thyroid functions. For example, and without limitation, status movement may include a positive trend, which may denote improved thyroid gland functioning, a negative trend, which may denote worsening and/or impaired thyroid gland functioning, and/or a neutral trend, which may denote no change and/or alteration to the previous functioning of the thyroid gland. Status movement may include determining an upper limit. As used in this disclosure an "upper limit" is a statistical limit that a thyroid enumeration may not exceed. For example, and without limitation upper limit may include a standard deviation maximum, a natural process limit, a maximum probability distribution, and the like thereof. As a further non-limiting example, upper limit 408 may include a limit that a thyroid enumeration may not be 3 standard deviations greater than a mean, range, proportion, probability, and the like thereof. Status movement may include determining an upper control. As used in this disclosure an "upper control" is a statistical warning that a thyroid enumeration may be diverging above a mean. For example, and without limitation upper control may include a standard deviation range, a natural process range, a probability distribution, and the like thereof. As a further non-limiting example, upper control may include a statistical warning that a thyroid enumeration may not be 2 standard deviations greater than a mean, range, proportion, probability, and the like thereof. Status movement may include determining a lower control. As used in this disclosure an "lower control" is a statistical warning that a thyroid enumeration may be diverging below a mean. For example, and without limitation lower control may include a standard deviation range, a natural process range, a probability distribution, and the like thereof. As a further non-limiting example, lower control may include a statistical warning that a thyroid enumeration may not be 2 standard deviations inferior to a mean, range, proportion, probability, and the like thereof. Status movement may include determining a lower limit. As used in this disclosure an "lower limit" is a statistical limit that a thyroid enumeration may not be inferior to. For example, and without limitation lower limit may include a standard deviation minimum, a natural process limit, a minimum probability distribution, and the like thereof. As a further non-limiting example, lower limit may include a limit that a thyroid enumeration may not be 3 standard deviations below a mean, range, proportion, probability, and the like thereof.

In an embodiment, and still referring to FIG. 1, status movement may be determined as a function of one or more rule sets. As used in this disclosure a "rule set" is a set of guidelines and/or rules to be followed to detect a signal and/or trend of the status movement. For example, and without limitation, rule set may include identifying a malfunction and/or malady as a function of a thyroid enumeration that exceeds and/or is inferior to upper limit and/or lower limit. In an embodiment, rule set may include identifying n number of consecutive thyroid enumerations that are all above and/or below a central mean, median, and/or mode. For example, 7 consecutive thyroid enumerations above the mean may indicate a trend in the thyroid function such as overproduction of one or more thyroid hormones. In yet another embodiment, rule set may include identifying n number of consecutive thyroid enumerations that are all increasing and/or decreasing. For example, 5 consecutive thyroid enumerations that are all decreasing may indicate a negative trend in the thyroid function such as decreased regulation of basal metabolic rate.

Still referring to FIG. 1, computing device 104 may identify thyroid status 112 as a function of producing a physiological influence as a function of vigor element. As used in this disclosure a "physiological influence" is an influence and/or impact a vigor element has on surrounding cells, tissues, and/or organs of an individual. For example, and without limitation, physiological influence may include an alteration on the brain as a function of the thyroid gland lack of production and/or secretion of T3, wherein a reduction of T3 may result in severe intellectual defects, abnormal balance, defects in fine motor skills, spasticity, deafness, and the like thereof. As a further non-limiting example, physiological influence may include an alteration in the skeletal system as a function of an overproduction and/or synthesis of calcitonin by the thyroid glands. In an embodiment, computing device 104 may determine physiological influence as a function of receiving an idealistic function. As used in this disclosure an "idealistic function" is a recommendation and/or guideline for an individual's biological system. As a non-limiting example, idealistic function may include a recommendation that a blood pressure should be 120/80 mmHg. As a further non-limiting example idealistic function may include a recommendation that a respiratory rate should be 14 breaths per minute. Idealistic function may include recommendations from one or more peer review sources such as scholarly peer reviews, government peer reviews, medical peer reviews, technical peer reviews, and the like thereof. Peer review sources may include, but are not limited to, Nature, The New England Journal of Medicine, The American Journal of Medicine, Journal of American Medical Association, The Lancet, and the like thereof. Idealistic function may include recommendations from one or more informed advisor associations, such as a source of one or more committees, organizations, and/or groups capable of determining and/or organizing recommendations and/or guidelines. As a non-limiting example informed advisor associations may include the American Medical Association, American Nurses Association, The Association for Accessible Medicines and the like thereof. Idealistic function may include recommendations from one or more medical websites that establish guidelines for the health status of individuals. As a non-limiting example, medical website may include, but are not limited to, UMDF, Medline Plus, Mayo Clinic, WebMD, Health.gov, and the like thereof.

Still referring to FIG. 1, computing device 104 may determine physiological influence as a function of idealistic function and thyroid enumeration 112 using a physiological machine-learning model. As used in this disclosure a "physiological machine-learning model" is a machine-learning model to produce a physiological influence output given idealistic functions and/or thyroid enumerations as inputs; this is in contrast to a non-machine learning software program where the commands to be executed are determined in advance by a user and written in a programming language. Physiological machine-learning model may include one or more physiological machine-learning processes such as supervised, unsupervised, or reinforcement machine-learning processes that computing device 104 and/or a remote device may or may not use in the determination of physiological influence, wherein a remote device is an external device to computing device 104 as described above in detail. A physiological machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train physiological machine-learning process as a function of a physiological training set. As used in this disclosure a "physiological training set" is a training set that correlates at least an idealistic function and a thyroid enumeration to a physiological influence. For example, and without limitation, idealistic function of a blood glucose level of 140 mg/dL and a thyroid enumeration 87 for calcitonin production may relate to a physiological influence of enhanced calcium concentrations. The physiological training set may be received as a function of user-entered valuations of idealistic functions, thyroid enumerations, and/or physiological influences. Computing device 104 may receive physiological training set by receiving correlations of idealistic functions and/or thyroid enumerations that were previously received and/or determined during a previous iteration of determining physiological influences. The physiological training set may be received by one or more remote devices that at least correlate an idealistic function and thyroid enumeration to a physiological influence, wherein a remote device is an external device to computing device 104, as described above. Physiological training set may be received in the form of one or more user-entered correlations of an idealistic function and/or thyroid enumeration to a physiological influence. Additionally or alternatively, a user may include an informed advisor, wherein an informed advisor may include, without limitation, thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive physiological machine-learning model from a remote device that utilizes one or more physiological machine learning processes, wherein remote device is described above in detail. For example, and without limitation, remote device may include a computing device, external device, processor, and the like thereof. Remote device may perform the physiological machine-learning process using the physiological training set to generate physiological influence and transmit the output to computing device 104. Remote device may transmit a signal, bit, datum, or parameter to computing device 104 that at least relates to physiological influence. Additionally or alternatively, the remote device may provide an updated machine-learning model. For example, and without limitation, an updated machine-learning model may be comprised of a firmware update, a software update, a physiological machine-learning process correction, and the like thereof. As a non-limiting example a software update may incorporate a new idealistic function that relates to a modified thyroid enumeration. Additionally or alternatively, the updated machine learning model may be transmitted to the remote device, wherein the remote device may replace the physiological machine-learning model with the updated machine-learning model and determine the physiological as a function of the thyroid enumeration using the updated machine-learning model. The updated machine-learning model may be transmitted by the remote device and received by computing device 104 as a software update, firmware update, or corrected physiological machine-learning model. For example, and without limitation a physiological machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, physiological machine-learning model may identify physiological influence as a function of one or more classifiers, wherein a classifier is described above in detail.

Still referring to FIG. 1, computing device 104 may determine a physiological fascicle as a function of physiological influence. As used in this disclosure a "physiological fascicle" is a group and/or bundle of physiological cells, tissues and/or organs that are affected and/or influenced. For example, and without limitation, physiological fascicle may determine that a physiological influence of a reduced sexual function may impact the thyroid system, reproductive system, circulatory system, excretory system, and the like thereof. As a further non-limiting example, physiological fascicle may determine that a physiological influence of reduced cognitive function may impact the thyroid system, neurological system, musculoskeletal system, and the like thereof. In an embodiment, and without limitation, thyroid status 112 may be determined as a function of the magnitude of the physiological fascicle. For example, and without limitation, a physiological fascicle that impacts 6 organs and/or systems may denote a low health status of the thyroid system, wherein a physiological fascicle that impacts 2 organs and/or systems may denote a medium health status of the thyroid system.

In an embodiment, and still referring to FIG. 1, computing device 104 may identify thyroid status 112 as a function of determining a probabilistic vector. As used in this disclosure a "probabilistic vector" is a data structure that represents one or more quantitative values and/or measures of probability associated with developing thyroid gland modifications. For example, and without limitation, probabilistic vector may indicate that an individual's thyroid gland function has a high probability of declining rapidly. As a further non-limiting example, probabilistic vector may indicate than an individual's thyroid gland function has a low probability of mutating. In an embodiment, and without limitation, a vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n}a_i^2}$, where $a_i$ is attribute number i of the vector. Scaling and/or normalization may function to make vector comparison independent of absolute quantities of attributes, while preserving any dependency on similarity of attributes.

In an embodiment, and still referring to FIG. 1, probabilistic vector may be determined as a function of a probabilistic machine-learning model. As used in this disclosure a "probabilistic machine-learning model" is a machine-learning model to produce a probabilistic vector output given vigor elements as inputs; this is in contrast to a non-machine learning software program where the commands to be executed are determined in advance by a user and written in a programming language. Probabilistic machine-learning model may include one or more probabilistic machine-learning processes such as supervised, unsupervised, or reinforcement machine-learning processes that computing device 104 and/or a remote device may or may not use in the determination of probabilistic vector, wherein a remote device is an external device to computing device 104 as described above in detail. A probabilistic machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train probabilistic machine-learning process as a function of a probabilistic training set. As used in this disclosure a "probabilistic training set" is a training set that correlates at least a vigor element to a probabilistic vector. For example, and without limitation, a vigor element of a mass in the thyroid gland relate to a probabilistic vector of 91 for the probability of developing a goiter. The probabilistic training set may be received as a function of user-entered valuations of vigor elements, and/or probabilistic vectors. Computing device 104 may receive probabilistic training set by receiving correlations of vigor elements and/or probabilistic vectors that were previously received and/or determined during a previous iteration of determining probabilistic vectors. The probabilistic training set may be received by one or more remote devices that at least correlate a vigor element to a probabilistic vector, wherein a remote device is an external device to computing device 104, as described above. Probabilistic training set may be received in the form of one or more user-entered correlations of a vigor element to a probabilistic vector. Additionally or alternatively, a user may include an informed advisor, wherein an informed advisor may include, without limitation, thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive probabilistic machine-learning model from a remote device that utilizes one or more probabilistic machine learning processes, wherein remote device is described above in detail. For example, and without limitation, remote device may include a computing device, external device, processor, and the like thereof. Remote device may perform the probabilistic machine-learning process using the probabilistic training set to generate probabilistic vector and transmit the output to computing device 104. Remote device may transmit a signal, bit, datum, or parameter to computing device 104 that at least relates to probabilistic vector. Additionally or alternatively, the remote device may provide an updated machine-learning model. For example, and without limitation, an updated machine-learning model may be comprised of a firmware update, a software update, a probabilistic machine-learning process correction, and the like thereof. As a non-limiting example a software update may incorporate a probabilistic vector that relates to a modified vigor element. Additionally or alternatively, the updated machine learning model may be transmitted to the remote device, wherein the remote device may replace the probabilistic machine-learning model with the updated machine-learning model and determine the probabilistic vector as a function of the vigor element using the updated machine-learning model. The updated machine-learning model may be transmitted by the remote device and received by computing device 104 as a software update, firmware update, or corrected probabilistic machine-learning model. For example, and without limitation a probabilistic machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, probabilistic machine-learning model may identify probabilistic vector as a function of one or more classifiers, wherein a classifier is described above in detail.

Still referring to FIG. 1, computing device 104 may produce thyroid status 112 by identifying a thyroid malady. As used in this disclosure a "thyroid malady" is an ailment and/or collection of ailments that impact an individual's thyroid gland. As a non-limiting example thyroid malady may include thyroid cancer, Graves' disease, Hashimoto's disease goiter, thyroid nodules, thyroid cancer, toxic adenomas, subacute thyroiditis, pituitary gland malfunctions, pituitary cancer, and the like thereof. Thyroid malady may be identified as a function of one or more malady machine-learning models. As used in this disclosure "malady machine-learning model" is a machine-learning model to produce a thyroid malady output given thyroid enumerations as inputs; this is in contrast to a non-machine learning software program where the commands to be executed are determined in advance by a user and written in a programming language. Malady machine-learning model may include one or more malady machine-learning processes such as supervised, unsupervised, or reinforcement machine-learning processes that computing device 104 and/or a remote device may or may not use in the determination of thyroid malady. A malady machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train malady machine-learning process as a function of a malady training set. As used in this disclosure "malady training set" is a training set that correlates at least a health system effect and thyroid enumeration 124 to a thyroid malady. As used in this disclosure "health system effect" is an impact and/or effect on the health system of an individual. For example, and without limitation, a health system effect may include muscle weakness, reduced sexual function, stunted brain development, reduced iodine transport, lethargy, and the like thereof. As a non-limiting example a thyroid enumeration of 87 and a health system effect of slowed heart rate may relate to a thyroid malady of Hashimoto's disease. The malady training set may be received as a function of user-entered valuations of thyroid enumerations, health system effects, and/or thyroid maladies. Computing device 104 may receive malady training by receiving correlations of thyroid enumerations and/or health system effects that were previously received and/or determined during a previous iteration of determining thyroid maladies. The malady training set may be received by one or more remote devices that at least correlate thyroid enumerations and/or health system effects to thyroid maladies, wherein a remote device is an external device to computing device 104, as described above. The malady training set may be received by one or more user-entered correlations of thyroid enumerations and health system effects to thyroid maladies. Additionally or alternatively, a user may include an informed advisor, wherein an informed advisor may include, without limitation, thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive malady machine-learning model from a remote device that utilizes one or more malady machine learning processes, wherein a remote device is described above in detail. For example, and without limitation, a remote device may include a computing device, external device, processor, and the like thereof. Remote device may perform the malady machine-learning process using the malady training set to generate thyroid malady and transmit the output to computing device 104. Remote device may transmit a signal, bit, datum, or parameter to computing device 104 that at least relates to thyroid maladies. Additionally or alternatively, the remote device may provide an updated machine-learning model. For example, and without limitation, an updated machine-learning model may be comprised of a firmware update, a software update, a malady machine-learning process correction, and the like thereof. As a non-limiting example a software update may incorporate a new thyroid enumeration that relates to a modified health system effect. Additionally or alternatively, the updated machine learning model may be transmitted to the remote device, wherein the remote device may replace the malady machine-learning model with the updated machine-learning model and determine the thyroid malady as a function of the thyroid enumeration using the updated machine-learning model. The updated machine-learning model may be transmitted by the remote device and received by computing device 104 as a software update, firmware update, or corrected malady machine-learning model. For example, and without limitation malady machine-learning model may utilize a neural net machine-learning process, wherein the updated machine-learning model may incorporate hierarchical clustering machine-learning process.

In an embodiment, and still referring to FIG. 1, computing device 104 may identify thyroid profile 128 by determining an autoimmune indicator. As used in this disclosure an "autoimmune indicator" is an element of data that denotes a presence and/or likelihood that an individual's immune system is attacking and/or destroying healthy body tissues by mistake. Autoimmune indicator may include one or more indicators such as HLA-B27, HLA-DR4, HLA-DR3, and the like thereof. As a further non-limiting example, autoimmune indicator may include one or more indicators such as, but not limited to, hemoglobin A1c (HbA1c), red blood cell magnesium, serum magnesium, complete blood count, red blood cell count, white blood cell count, vitamin D, ferritin, cortisol, high sensitivity C reactive protein (hsCRP), alanine aminotransferase (ALT), glucose, hemoglobin A1c, DHEAS, and/or testosterone. Autoimmune indicator may include any autoimmune indicator used as an autoimmune indicator as described in U.S. Nonprovisional application Ser. No. 17/007,318, filed on Aug. 31, 2020, and entitled "SYSTEM AND METHOD FOR REPRESENTING AN ARRANGED LIST OF PROVIDER ALIMENT POSSIBILITIES," the entirety of which is incorporated herein by reference.

In an embodiment, and still referring to FIG. 1, computing device 104 may identify thyroid status 112 by determining an autoimmune indicator. As used in this disclosure an "autoimmune indicator" is an element of data that denotes a presence and/or likelihood that an individual's immune system is attacking and/or destroying healthy body tissues by mistake. Autoimmune indicator may include one or more indicators such as TSHm FT4, anti-TPO, anti-Tg, and the like thereof. Autoimmune indicator may include any autoimmune indicator used as an autoimmune indicator as described in U.S. Nonprovisional application Ser. No. 17/007,318, filed on Aug. 31, 2020, and entitled "SYSTEM AND METHOD FOR REPRESENTING AN ARRANGED LIST OF PROVIDER ALIMENT POSSIBILITIES," the entirety of which is incorporated herein by reference.

Still referring to FIG. 1, computing device 104 determines an edible 132 as a function of thyroid status 112. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. In an embodiment, edible may be determined as a function of physiological response, wherein a first edible may be identified for a first physiological response and a second edible may be determined for a second physiological response. For example, and without limitation, a first edible of steak may be determined for a first physiological response of clinical depression, wherein a second edible of pineapples may be identified for a second physiological response of serotonin reduction. Computing device 104 may determine edible 132 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an "edible directory" is a database of edibles that may be identified as a function of one or more metabolic components, as described in detail below, in reference to FIG. 3.

Still referring to FIG. 1, computing device 104 may produce a nourishment desideration as a function of thyroid status 112. As used in this disclosure a "nourishment desideration" is requirement and/or necessary amount of nutrients required for a user to consume. As a non-limiting example, nourishment desideration may include a user requirement of 10 mg of zinc to be consumed per day. Nourishment desideration may be determined as a function of receiving a nourishment goal. As used in this disclosure a "nourishment goal" is a recommended amount of nutrients that a user should consume. Nourishment goal may be identified by one or more organizations that relate to, represent, and/or study thyroid glands in humans, such as the American Medical Association, American Autoimmune Related Diseases Association, Thyroid Cancer Survivors' Association, The Light of Life Foundation, ThyroidChange, American Thyroid Association, Graves' Disease and Thyroid Foundation, The Magic Foundation, and the like thereof.

Still referring to FIG. 1, computing device 104 identifies edible 132 as a function of nourishment composition, nourishment desideration, and an edible machine-learning model. As used in this disclosure a "edible machine-learning model" is a machine-learning model to produce an edible output given nourishment compositions and nourishment desiderations as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 132, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment desideration to an edible. For example, and without limitation, nourishment composition of 50 mcg of selenium and a nourishment desideration of 23 mcg of selenium as a function of hyperthyroidism may relate to an edible of shellfish. The edible training set may be received as a function of user-entered valuations of nourishment compositions, nourishment desiderations, and/or edibles. Computing device 104 may receive edible training set by receiving correlations of nourishment compositions and/or nourishment desiderations that were previously received and/or determined during a previous iteration of determining edibles. The edible training set may be received by one or more remote devices that at least correlate a nourishment composition and nourishment desideration to an edible, wherein a remote device is an external device to computing device 104, as described above. Edible training set may be received in the form of one or more user-entered correlations of a nourishment composition and/or nourishment desideration to an edible. Additionally or alternatively, a user may include an informed advisor, wherein an informed advisor may include, without limitation thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 132 and transmit the output to computing device 104. Remote device may transmit a signal, bit, datum, or parameter to computing device 104 that at least relates to edible 132. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment desideration. Additionally or alternatively, the updated machine learning model may be transmitted to the remote device, wherein the remote device may replace the edible machine-learning model with the updated machine-learning model and determine the edible as a function of the nourishment desideration using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Non-provisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, edible machine-learning model may identify edible 132 as a function of one or more classifiers, wherein a classifier is described above in detail.

Still referring to FIG. 1, computing device 104 may identify edible as a function of a likelihood parameter. As used in this disclosure a "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of spinach. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for cinnamon flavor and/or crunchy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database or other data structure including flavors for an edible. As a non-limiting example flavor directory may include a list and/or collection of edibles that all contain sweet flavor variables. As a further non-limiting example flavor directory may include a list and/or collection of edibles that all contain sour flavor variables. Flavor directory may be implemented similarly to an edible directory as described below in detail, in reference to FIG. 3. Likelihood parameter may alternatively or additionally include any user taste profile and/or edible profile used as a likelihood parameter as described in U.S. Non-provisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 136 as a function of edible 132. As used in this disclosure a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 136 may consist of recommending carrots for 8 days. As a further non-limiting example nourishment program 136 may recommend bread for a first day, pine nuts for a second day, and fish for a third day. Nourishment program 136 may include one or more diet programs such as autoimmune protocol, paleo, keto, vegan, vegetarian, Mediterranean, Dukan, Zone, HCG, and the like thereof. Computing device 104 may develop nourishment program 136 as a function of a thyroid functional goal. As used in this disclosure an "thyroid functional goal" is a goal that an edible may generate according to a predicted and/or purposeful plan. As a non-limiting example, thyroid functional goal may include a treatment goal. As used in this disclosure a "treatment goal" is a thyroid functional goal that is designed to at least reverse and/or eliminate vigor element 108, thyroid status 112, and/or thyroid malady. As a non-limiting example, a treatment goal may include reversing the effects of the thyroid malady thyroiditis. As a further non-limiting example, a treatment goal includes reversing the thyroid malady Grave's disease. Thyroid functional goal may include a prevention goal. As used in this disclosure a "prevention goal" is a thyroid functional goal that is designed to at least prevent and/or avert vigor element 108, thyroid status 112, and/or thyroid malady. As a non-limiting example, a prevention goal may include preventing the development of the thyroid malady Hashimoto's disease. Thyroid functional goal may include a mitigation goal. As used in this disclosure a "mitigation goal" is a functional goal that is designed to reduce the symptoms and/or effects of a thyroid malady. For example, and without limitation, mitigation goal may include reducing the effects of cognitive dysfunction due to hypothyroidism. Additionally or alternatively, thyroid functional goal may include one or more goals associated with epigenetic alteration and/or gene therapy to alter a mutation and/or modification of an individual's nuclear code.

Still referring to FIG. 1, computing device 104 may develop nourishment program 136 as a function of edible 132 and thyroid functional goal using a nourishment machine-learning model. As used in this disclosure a "nourishment machine-learning model" is a machine-learning model to produce a nourishment program output given edibles and/or thyroid functional goals as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 136. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a thyroid functional goal to an edible. The nourishment training set may be received as a function of user-entered edibles, thyroid functional goals, and/or nourishment programs. For example, and without limitation, a thyroid functional goal of treating postpartum thyroiditis may correlate to an edible of chicken. Computing device 104 may receive nourishment training by receiving correlations of thyroid functional goals and/or edibles that were previously received and/or determined during a previous iteration of developing nourishment programs. The nourishment training set may be received by one or more remote devices that at least correlate a thyroid functional goal and/or edible to a nourishment program, wherein a remote device is an external device to computing device 104, as described above. Nourishment training set may be received in the form of one or more user-entered correlations of a thyroid functional goal and/or edible to a nourishment program. Additionally or alternatively, a user may include an informed advisor, wherein an informed advisor may include, without limitation thyroidologists, family physicians, endocrinologists, gastroenterologists, internists, oncologists, pediatricians, cardiologists, geneticists, neurologists, physical therapists, primary care providers, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 136 and transmit the output to computing device 104. The remote device may transmit a signal, bit, datum, or parameter to computing device 104 that at least relates to nourishment program 136. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new thyroid functional goal that relates to a modified edible. Additionally or alternatively, the updated machine learning model may be transmitted to the remote device, wherein the remote device may replace the nourishment machine-learning model with the updated machine-learning model and develop the nourishment program as a function of the thyroid functional goal using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
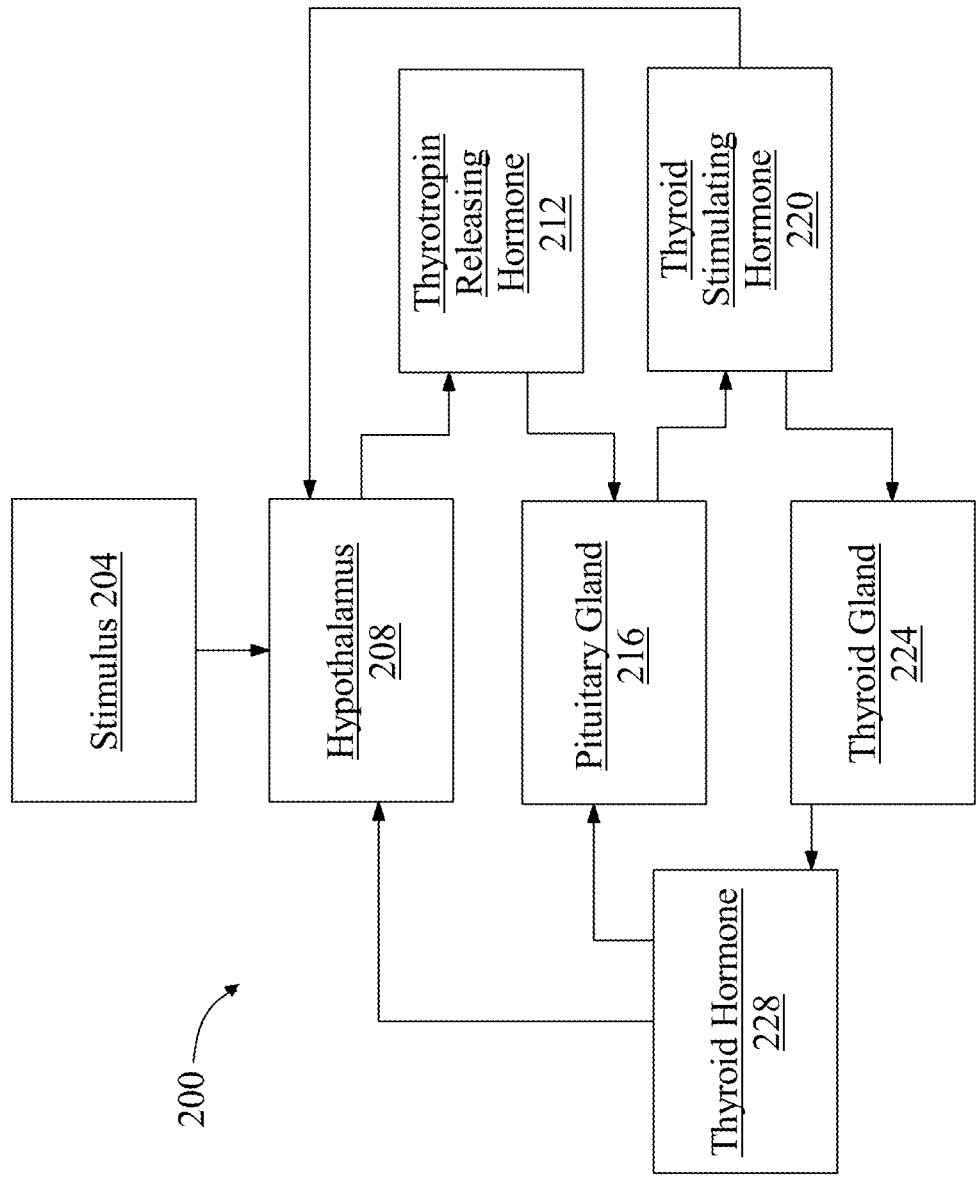
FIG. 2 is a block diagram of an exemplary embodiment of a homeostatic mechanism according to an embodiment of the invention.

Now referring to FIG. 2, an exemplary embodiment 200 of a homeostatic element 116 is illustrated. In an embodiment homeostatic element 116 may include a stimulus 204. As used in this disclosure a "stimulus" is an action, entity, and/or object that evokes a functional reaction and/or change in the biological system of an individual. For example, and without limitation, stimulus 204 may include a touch, smell, taste, sound, visually observed object, vestibular movement, proprioceptive signal, and the like thereof. Stimulus 204 may stimulate a hypothalamus 208. As used in this disclosure a "hypothalamus" is a region of the forebrain below the thalamus. In an embodiment hypothalamus may secret one or more hormones that control and/or regulate one or more glands. For example, and without limitation hypothalamus may include a region that secretes a thyrotropin releasing hormone 212. As used in this disclosure a "thyrotropin releasing hormone" is a hypophysiotropic hormone. For example, and without limitation, thyrotropin releasing hormone 212 may stimulate a pituitary gland 216. As used in this disclosure a "pituitary gland" is an endocrine gland located below the hypothalamus. In an embodiment pituitary gland 216 may synthesize and/or secret hormones to target organs and/or tissues in the human body. For example, and without limitation pituitary gland 216 may secrete one or more hormones such as somatotropes, corticotropes, thyrotropes, gonadotropes, lactotropes, and the like thereof. In an embodiment and without limitation, pituitary gland 216 may secrete a thyroid stimulating hormone 220. As used in this disclosure a "thyroid stimulating hormone" is a pituitary hormone. In an embodiment, thyroid stimulating hormone 220 may interact with hypothalamus 208 as a function of a negative feedback loop. As used in this disclosure a "negative feedback loop" is a feedback system wherein an output signals to the process and/or mechanism to stop producing the output. For example, and without limitation, thyroid stimulating hormone 220 may signal to hypothalamus 208 to reduce the production and/or secretion of thyrotropin releasing hormone 212 of hypothalamus 208. In another embodiment, thyroid stimulating hormone 220 may stimulate a thyroid gland 224. As used in this disclosure a "thyroid gland" is an endocrine gland in the neck consisting of two connected lobes. Thyroid gland 224 may be composed of two lobes that are connected by a narrow tissue band. Thyroid gland 224 may be composed of follicles, follicular cells, parafollicular cells, and the like thereof. In an embodiment, and without limitation, thyroid gland 224 may produce a thyroid hormone 228. As used in this disclosure a "thyroid hormone" is a tyrosine-based hormone released by the thyroid gland. Thyroid hormone 228 may include one or more hormones such as triiodothyronine (T3) and/or thyroxine (T4). Thyroid hormone 228 may include one or more functions to increase cardiac output, increase heart rate, increase ventilation rate, increase basal metabolic rate, potentiate the effects of catecholamines, potentiate brain development, thicken the endometrium, increase catabolism of proteins and/or carbohydrates, and the like thereof. In an embodiment, and without limitation thyroid hormone 228 may interact with hypothalamus 208 and/or pituitary gland 216 as a function of a negative feedback loop, wherein a negative feedback loop is described above. For example, and without limitation thyroid hormone 228 may interact with hypothalamus 208 to reduce the production and/or secretion of thyrotropin release hormone 212, which reduces both the production and/or secretion of thyroid stimulating hormone 220 and thyroid hormone 228. As a further non-limiting example, thyroid hormone 228 may interact with pituitary gland 216 to reduce the production and/or secretion of thyroid stimulation hormone 220, which reduces the production and/or secretion of thyroid hormone 228.

Figure 3:
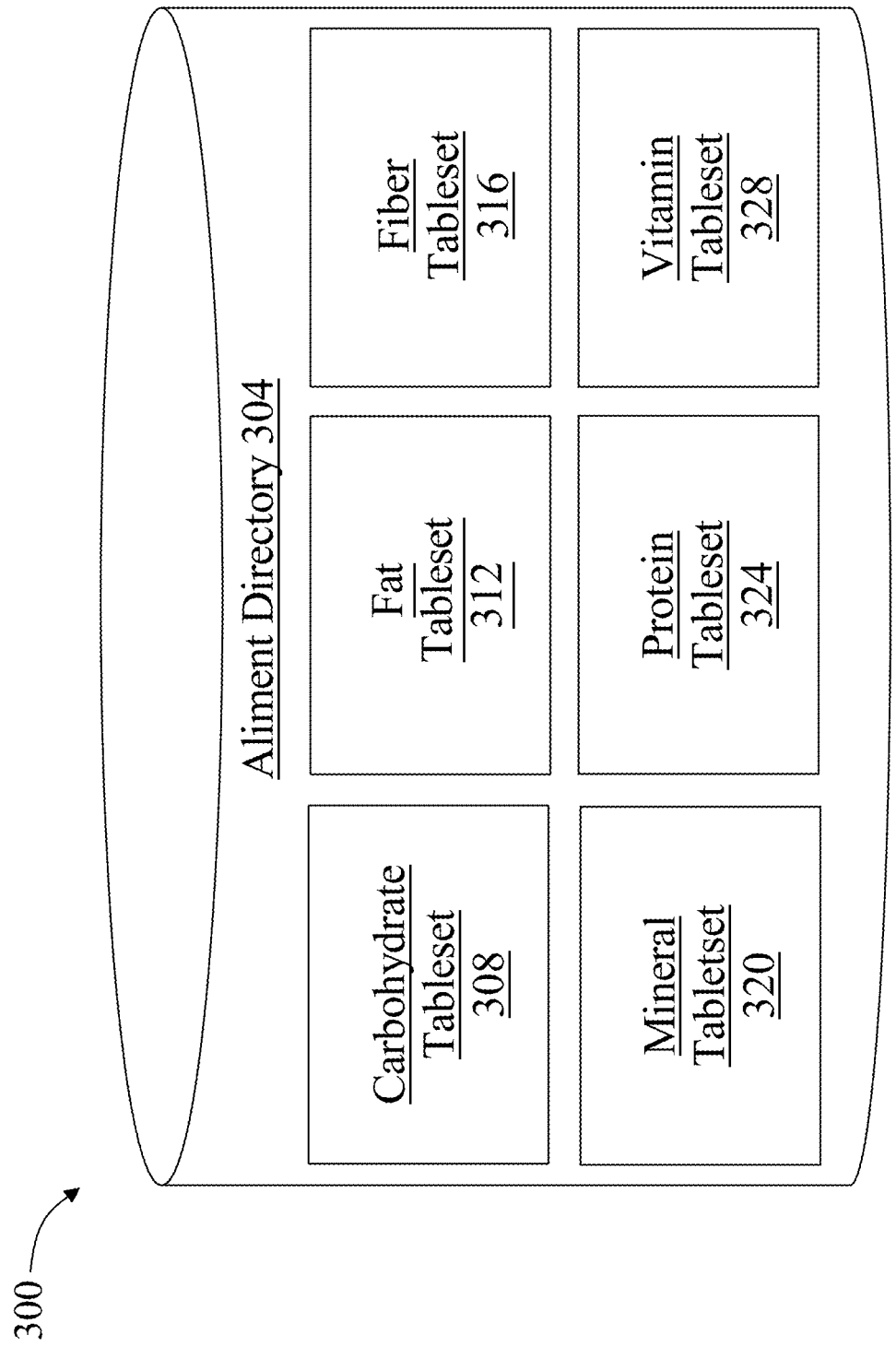
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
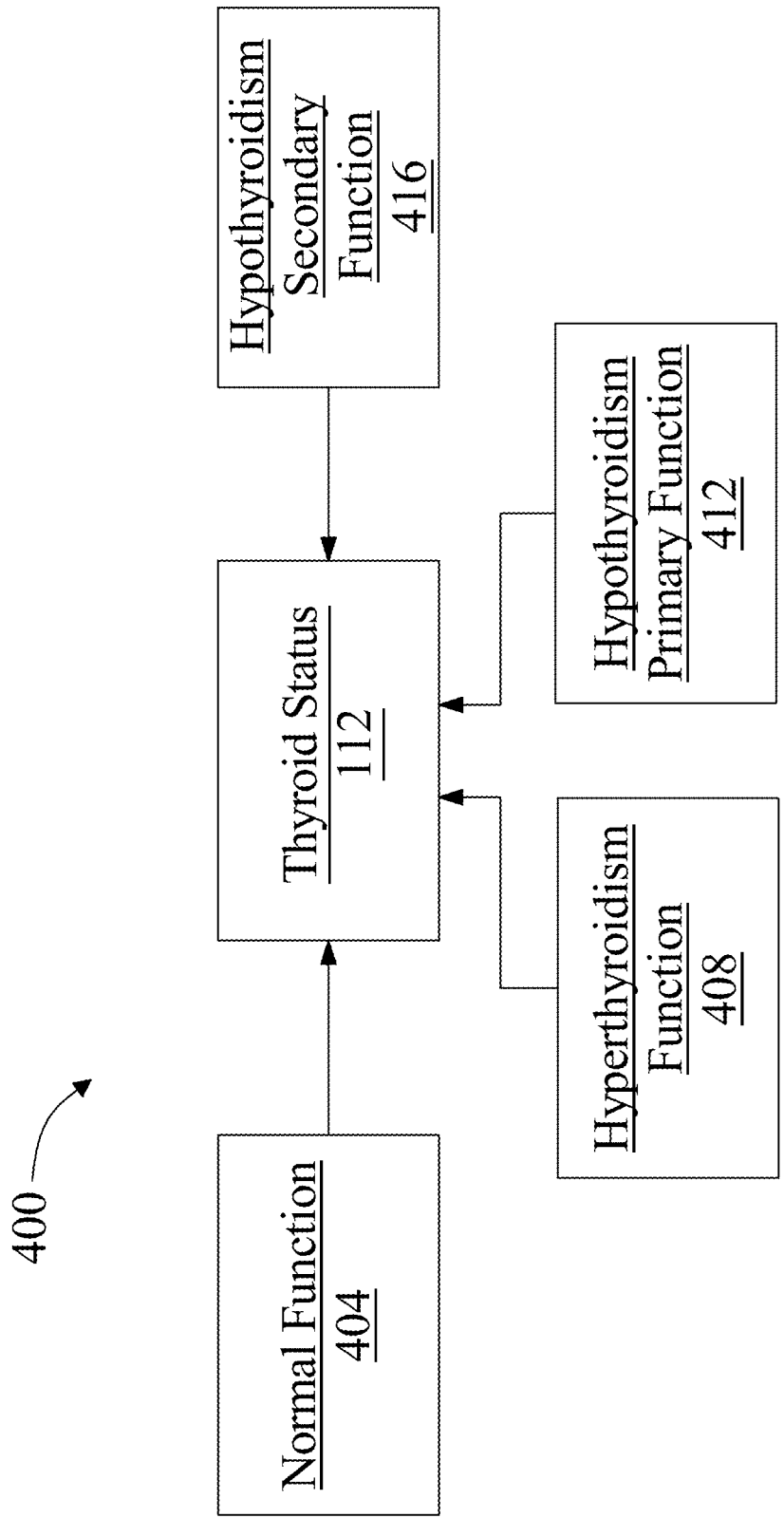
FIG. 4 is a block diagram of an exemplary embodiment of a thyroid status according to an embodiment of the invention.

Now referring to FIG. 4, an exemplary embodiment 400 of thyroid status 112. In an embodiment thyroid status may include a normal function 404. As used in this disclosure a "normal function" is an expected function of a thyroid gland. For example, and without limitation, normal function 404 may include one or more thyroid stimulating hormone concentration ranges such as 0.4-5.49 mIU/L. As a further non-limiting example, normal function 404 may include one or more T3 ranges between 100-200 nanograms per deciliter. As a further non-limiting example, normal function 404 may include one or more T4 ranges between 5-12 micrograms per deciliter. Thyroid status 112 may include a hyperthyroidism function 408. As used in this disclosure a "hyperthyroidism function" is a function of the thyroid gland wherein there is a low production of TSH and an overproduction of thyroid hormones. For example, and without limitation, hyperthyroidism function 408 may include a function wherein a concentration of 0.17 mIU/L of TSH is produced, wherein a concentration of 400 nanograms per deciliter of T3 is produced. As a further non-limiting example, hyperthyroidism function 408 may include a function wherein a concentration of 0.23 mIU/L of TSH is produced, wherein a concentration of 16 micrograms per deciliter of T4 is produced. Thyroid status 112 may include a hypothyroidism primary function 412. As used in this disclosure a "hypothyroidism primary function" is a function of the thyroid gland wherein there is a high production of TSH and a low production of thyroid hormones. For example, and without limitation, hypothyroidism primary function 412 may include a function wherein a concentration of 7.2 mIU/L of TSH is produced, wherein a concentration 25 nanograms per deciliter of T3 is produced. As a further non-limiting example, hypothyroidism primary function 412 may include a function wherein a concentration of 6.1 mIU/L of TSH is produced, wherein a concentration of 2 micrograms per deciliter of T4 is produced. Thyroid status 112 may include a hypothyroidism secondary function 416. As used in this disclosure a "hypothyroidism secondary function" is a function of the thyroid gland wherein there is a low production of TSH and a low production of thyroid hormones. For example, and without limitation, hypothyroidism secondary function 416 may include a function wherein a concentration of 0.1 mIU/L of TSH is produced, wherein a concentration 13 nanograms per deciliter of T3 is produced. As a further non-limiting example, hyperthyroidism secondary function 416 may include a function wherein a concentration of 0.17 mIU/L of TSH is produced, wherein a concentration of 0.9 micrograms per deciliter of T4 is produced.

Figure 5:
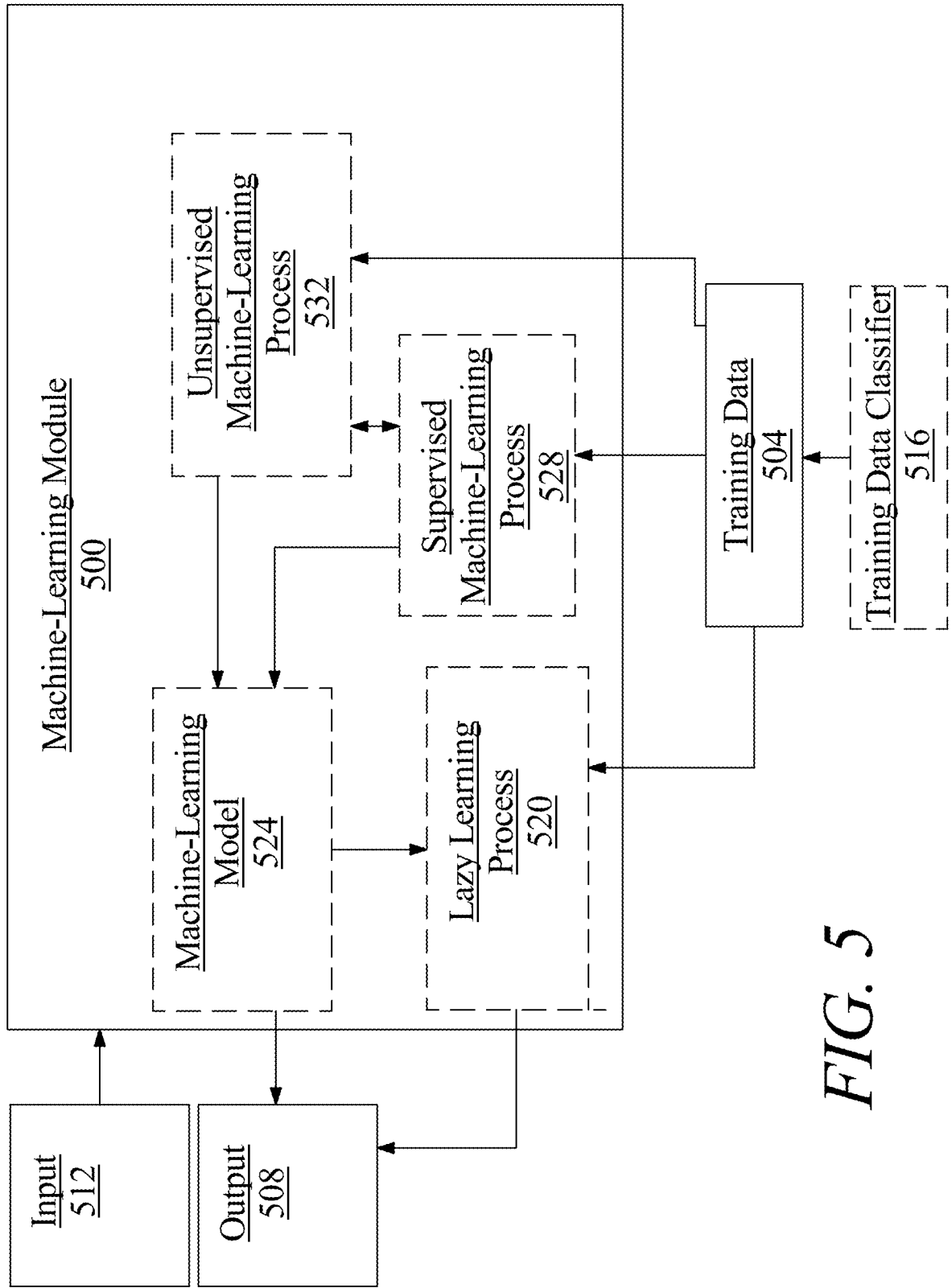
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs of homeostatic elements and/or thyroid enumerations may result in a thyroid status output.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of homeostatic elements such as processes associated with the hypothalamus, pituitary, thyroid, parathyroids, thyroids, pineal bodies, ovaries, testes, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include homeostatic elements and/or thyroid enumerations as described above as inputs, thyroid statuses as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
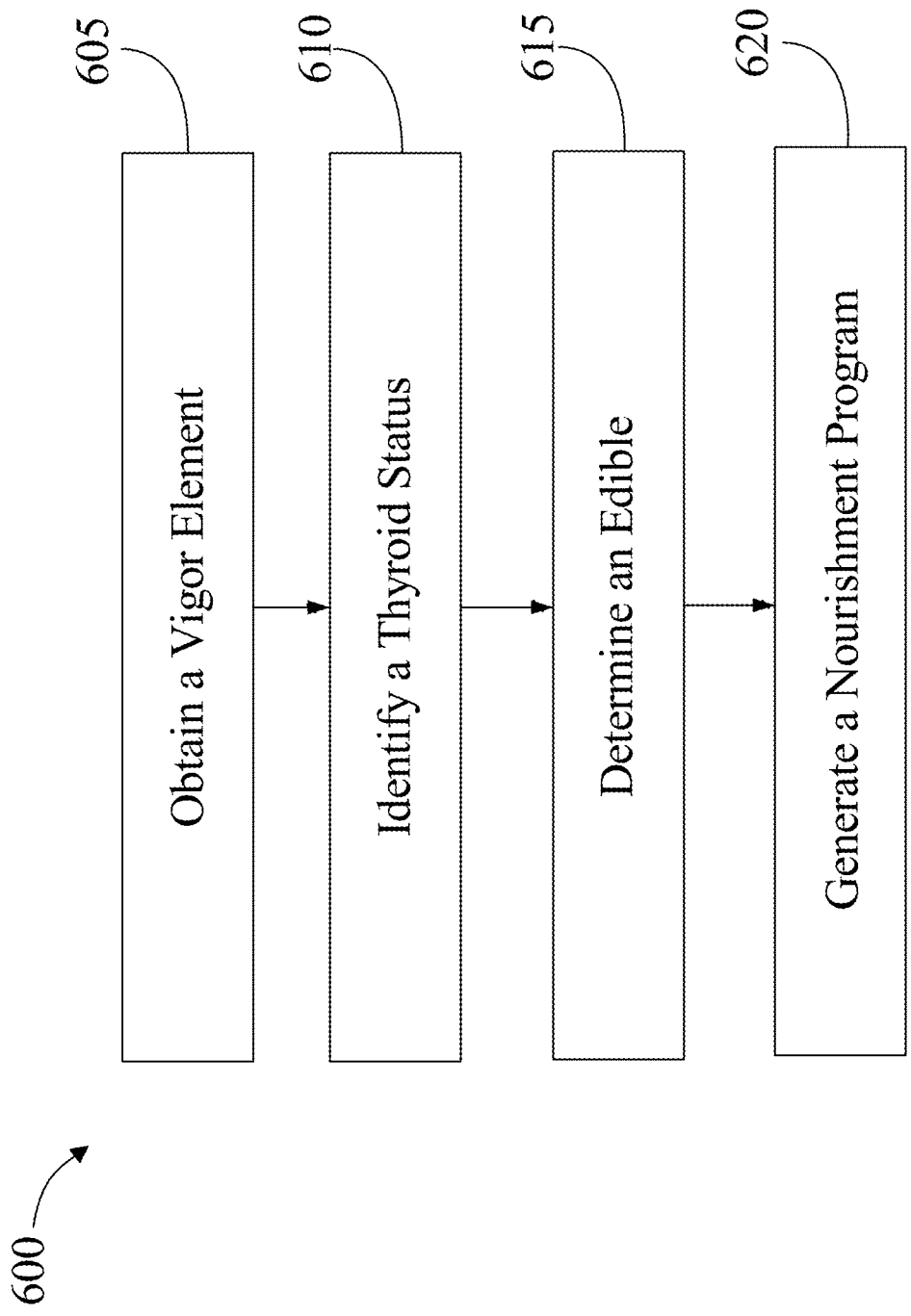
FIG. 6 is a process flow diagram illustrating an exemplary embodiment of a method of generating a thyroid malady nourishment program.

Now referring to FIG. 6, an exemplary embodiment 600 of a method for generating a thyroid malady nourishment program is illustrated. At step 605, a computing device 104 obtains a vigor element 108. Computing device 104 includes any of the computing device 104 as described above, in reference to FIGS. 1-5. Vigor element 108 includes any of the vigor element 108 as described above, in reference to FIGS. 1-5.

Still referring to FIG. 6, at step 610, computing device 104 identifies a thyroid status 112. Thyroid status 112 includes any of the thyroid status 112 as described above, in reference to FIGS. 1-5. Computing device 104 identifies thyroid status 112 as a function of obtaining a homeostatic element 116. Homeostatic element 116 includes any of the homeostatic element 116 as described above, in reference to FIGS. 1-5. Homeostatic element 116 is obtained as a function of a vigor database 120. Vigor database 120 includes any of the vigor database 120 as described above, in reference to FIGS. 1-5. Computing device 104 identifies thyroid status 112 as a function of producing a thyroid enumeration 124 as a function of vigor element 108. Thyroid enumeration 124 includes any of the thyroid enumeration 124 as described above, in reference to FIGS. 1-5. Computing device 104 identifies thyroid status as a function of homeostatic element 116 and thyroid enumeration 124 using a status machine-learning model 128. Status machine-learning model 128 includes any of the status machine-learning model 128 as described above, in reference to FIGS. 1-5.

Still referring to FIG. 6, at step 615, computing device 104 determines an edible 132 as a function of thyroid status 112. Edible 132 includes any of the edible 132 as described above, in reference to FIGS. 1-5.

Still referring to FIG. 6, at step 620, computing device 104 generates a nourishment program 136 as a function of edible 132. Nourishment program 136 includes any of the nourishment program 136 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
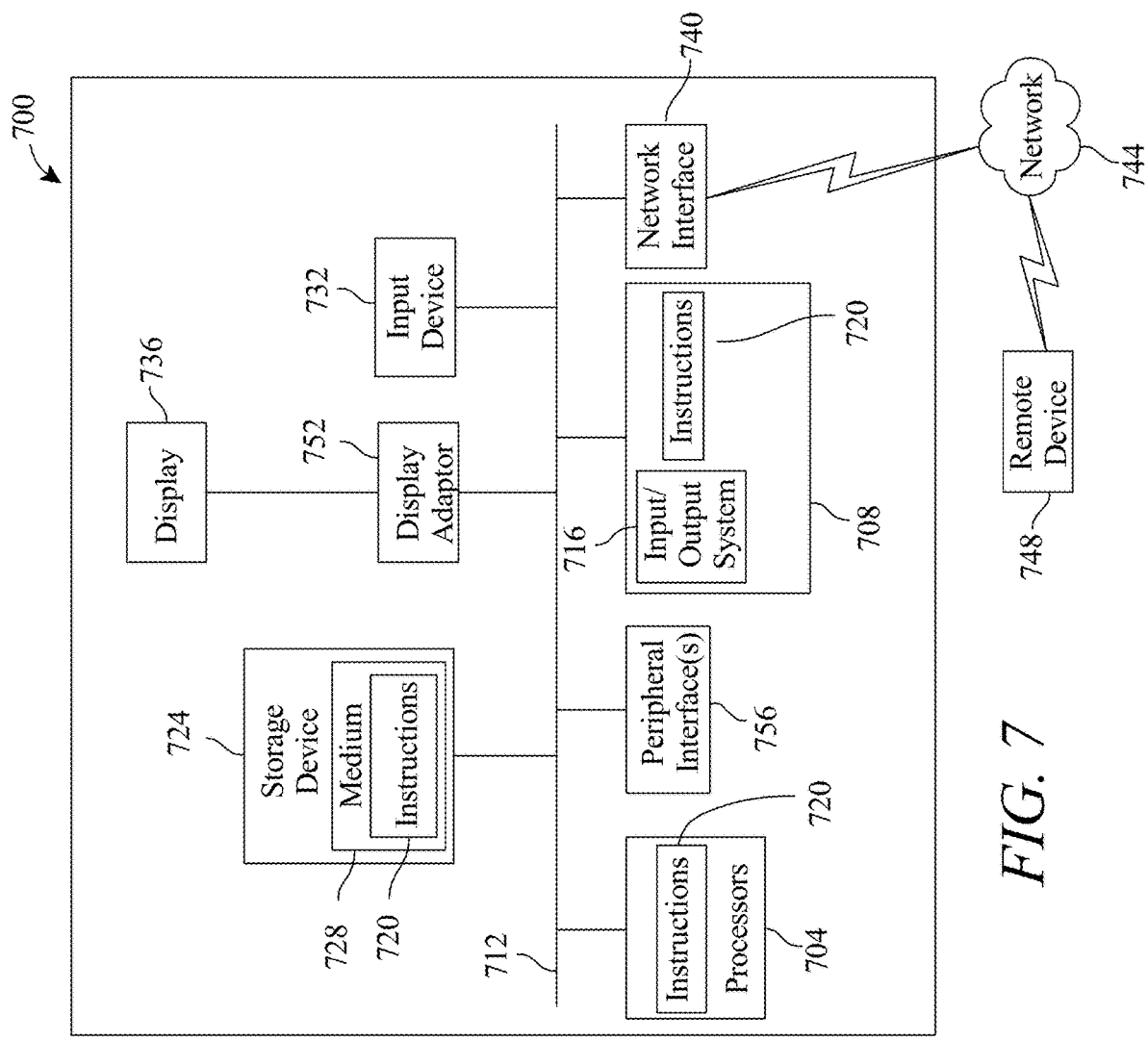
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a thyroid malady nourishment program, the system comprising:
    at least a computing device, the at least a computing device configured to:
        obtain, from a collection device, a vigor element, wherein the vigor element comprises a biological sample datum collected from a user;
        identify a thyroid status as a function of the vigor element, wherein identifying the thyroid status further comprises:
            obtaining a homeostatic element from a vigor database;
            producing a thyroid enumeration as a function of the vigor element including the biological sample datum collected from the user; and
            identifying the thyroid status as a function of the homeostatic element and the thyroid enumeration using a status machine-learning model, wherein using the status machine-learning model further comprises:
                generating a status training set using a training data classifier to classify elements of the training set to specific sub-categories of homeostatic elements with each governing a specific health adjustment mechanism;
                training, iteratively, the status machine-learning model as a function of at least one sub-category of the status training set and a supervised machine-learning algorithm, wherein the status training set correlates homeostatic element data and thyroid enumeration data to thyroid status data based on the clustered data therein, wherein the supervised machine-learning algorithm uses the status training set in conjunction with a scoring function to detect and generate a desired form of relationship between elements of the homeostatic element data, thyroid enumeration data and thyroid status data, and wherein training the status machine-learning model comprises utilizing results generated by iterative operation of the status machine-learning model;
                generating, as a function of the homeostatic element, the thyroid enumeration and the iteratively trained status machine-learning model, the thyroid status;
        determine at least one edible as a function of the thyroid status, a physiological response, and a likelihood parameter based on a taste profile of the user, wherein determining the at least one edible comprises:
            determining at least a first edible for a first physiological response; and
            determining at least a second edible for at least a second physiological response, wherein the at least a second physiological response is different than the first physiological response;
        generate a nourishment program as a function of at least the first and second edible, wherein the nourishment program provides a frequency and duration consumption plan of at least the first and second edible for the user;
        provide the nourishment program as a stimulus to a patient user; and
        determining an effect of the nourishment program to the thyroid status of a patient user as a function of an updated homeostatic element resulting from the nourishment program.

2. The system of claim 1, wherein obtaining the vigor element further comprises receiving a proneness indicator and obtaining the vigor element as a function of the proneness indicator.

3. The system of claim 1, wherein identifying the thyroid status further comprises:
    identifying a statistical deviation, wherein the statistical deviation comprises a measure of difference between the thyroid enumeration and homeostatic element; and
    producing the thyroid status as a function of the statistical deviation.

4. The system of claim 1, wherein identifying the thyroid status further comprises determining a status movement and identifying the thyroid status as a function of the status movement.

5. The system of claim 1, wherein identifying the thyroid status further comprises:
    producing a physiological influence as a function of the vigor element;
    determining a physiological fascicle as a function of the physiological influence; and
    identifying the thyroid status as a function of the physiological fascicle.

6. The system of claim 1, wherein producing the thyroid enumeration further comprises:
    determining an origin of malfunction; and
    producing the thyroid enumeration as a function of the vigor element and the origin of malfunction using an origin machine-learning model.

7. The system of claim 1, wherein identifying the thyroid status further comprises:
    determining a probabilistic vector, wherein the probabilistic vector comprises a data representing one or more quantitative measures of probability associated with developing thyroid gland modifications; and
    identifying the thyroid status as a function of the probabilistic vector.

8. The system of claim 1, wherein identifying the thyroid status includes determining a thyroid malady and producing the thyroid status as a function of the thyroid malady.

9. The system of claim 1, wherein identifying the thyroid status further comprises:
    determining an autoimmune element; and
    identifying the thyroid status as a function of the autoimmune element.

10. The system of claim 1, wherein generating the nourishment program further comprises:
    obtaining a thyroid functional goal; and generating the nourishment program as a function of the thyroid functional goal and the edible using a nourishment machine-learning model.

11. A method for generating a thyroid malady nourishment program, the method comprising:

obtaining, by at least a computing device from a collection device, a vigor element, wherein the vigor element comprises a biological sample collected from a user;

identifying, by the computing device, a thyroid status as a function of the vigor element, wherein identifying the thyroid status further comprises:

obtaining a homeostatic element from a vigor database;

producing a thyroid enumeration as a function of the vigor element including the biological sample datum collected from the user; and identifying the thyroid status as a function of the homeostatic element and the thyroid enumeration using a status machine-learning model, wherein using the status machine-learning model further comprises:

generating a status training set using a training data classifier to classify elements of the training set to specific sub-categories of homeostatic elements with each governing a specific health adjustment mechanism;

training, iteratively, the status machine-learning model as a function of at least one sub-category of the status training set and a supervised machine-learning algorithm, wherein the status training set correlates homeostatic element data and thyroid enumeration data to thyroid status data based on the clustered data therein, wherein the supervised machine-learning algorithm uses the status training set in conjunction with a scoring function to detect and generate a desired form of relationship between elements of the homeostatic element data, thyroid enumeration data and thyroid status data, and wherein training the status machine-learning model comprises utilizing results generated by iterative operation of the status machine-learning model;

generating, as a function of the homeostatic element, the thyroid enumeration and the iteratively trained status machine-learning model, the thyroid status;

determining, by the computing device, at least one edible as a function of the thyroid status, a physiological response, and a likelihood parameter based on a taste profile of the user, wherein determining the at least one edible comprises:

determining at least a first edible for a first physiological response; and determining at least a second edible for at least a second physiological response, wherein the at least a second physiological response is different than the first physiological response;

generating, by the computing device, a nourishment program as a function of at least the first and second edible wherein the nourishment program provides a frequency and duration consumption plan of at least the first and second edible for the user;

provide the nourishment program as a stimulus to a patient user; and determining an effect of the nourishment program to the thyroid status of a patient user as a function of an updated homeostatic element resulting from the nourishment program.

12. The method of claim 11, wherein obtaining the vigor element further comprises receiving a proneness indicator and obtaining the vigor element as a function of the proneness indicator.

13. The method of claim 11, wherein identifying the thyroid status further comprises:

identifying a statistical deviation, wherein the statistical deviation comprises a measure of difference between the thyroid enumeration and homeostatic element; and producing the thyroid status as a function of the statistical deviation.

14. The method of claim 11, wherein identifying the thyroid status further comprises determining a status movement and identifying the thyroid status as a function of the status movement.

15. The method of claim 11, wherein identifying the thyroid status further comprises:

producing a physiological influence as a function of the vigor element;

determining a physiological fascicle as a function of the physiological influence; and identifying the thyroid status as a function of the physiological fascicle.

16. The method of claim 11, wherein producing the thyroid enumeration further comprises:

determining an origin of malfunction; and producing the thyroid enumeration as a function of the vigor element and the origin of malfunction using an origin machine-learning model.

17. The method of claim 11, wherein identifying the thyroid status further comprises:

determining a probabilistic vector, wherein the probabilistic vector comprises a data representing one or more quantitative measures of probability associated with developing thyroid gland modifications; and identifying the thyroid status as a function of the probabilistic vector.

18. The method of claim 11, wherein identifying the thyroid status includes determining a thyroid malady and producing the thyroid status as a function of the thyroid malady.

19. The method of claim 11, wherein identifying the thyroid status further comprises:

determining an autoimmune element; and identifying the thyroid status as a function of the autoimmune element.

20. The method of claim 11, wherein generating the nourishment program further comprises:

obtaining a thyroid functional goal; and generating the nourishment program as a function of the thyroid functional goal and the edible using a nourishment machine-learning model.

* * * * *